(12) United States Patent
Littrup et al.

(10) Patent No.: US 10,278,672 B2
(45) Date of Patent: *May 7, 2019

(54) METHOD OF CHARACTERIZING THE PATHOLOGICAL RESPONSE OF TISSUE TO A TREATMENT PLAN

(71) Applicant: Delphinus Medical Technologies, Inc., Plymouth, MI (US)

(72) Inventors: Peter John Littrup, Plymouth, MI (US); Nebojsa Duric, Plymouth, MI (US)

(73) Assignee: Delphinus Medical Technologies, Inc., Novi, MI (US)

( * ) Notice: Subject to any disclaimer, the term of this patent is extended or adjusted under 35 U.S.C. 154(b) by 683 days.

This patent is subject to a terminal disclaimer.

(21) Appl. No.: 14/835,349

(22) Filed: Aug. 25, 2015

(65) Prior Publication Data

US 2015/0359508 A1 Dec. 17, 2015

Related U.S. Application Data

(63) Continuation of application No. 13/027,036, filed on Feb. 14, 2011, now Pat. No. 9,144,403.

(Continued)

(51) Int. Cl.
  *A61B 8/08* (2006.01)
  *G06T 7/00* (2017.01)
  (Continued)

(52) U.S. Cl.
  CPC ............ *A61B 8/085* (2013.01); *A61B 5/4848* (2013.01); *A61B 8/0825* (2013.01);
  (Continued)

(58) Field of Classification Search
  None
  See application file for complete search history.

(56) References Cited

U.S. PATENT DOCUMENTS

| 3,154,067 A | 10/1964 | Stenstrom et al. |
| 3,771,355 A | 11/1973 | Sachs |

(Continued)

FOREIGN PATENT DOCUMENTS

| CA | 2324602 A | 9/1999 |
| EP | 284055 A | 9/1988 |

(Continued)

OTHER PUBLICATIONS

EP11742965.4 Extended Search Report dated Jun. 27, 2013.

(Continued)

*Primary Examiner* — Katherine Fernandez

(74) *Attorney, Agent, or Firm* — Wilson Sonsini Goodrich & Rosati

(57) ABSTRACT

A method of characterizing the pathological response of tissue to a treatment plan, including: obtaining a set of sequential morphology renderings of the tissue, wherein each rendering corresponds to a particular point in time during the treatment plan; generating a set of representative values of a biomechanical property of the tissue for the set of renderings, wherein each representative value is based on a corresponding rendering; determining a trend of the biomechanical property based on the set of representative values; and predicting response of the tissue to the treatment plan based on the trend of the biomechanical property.

20 Claims, 5 Drawing Sheets

Related U.S. Application Data

(60) Provisional application No. 61/304,256, filed on Feb. 12, 2010.

(51) Int. Cl.
*A61B 8/00* (2006.01)
*A61B 5/00* (2006.01)

(52) U.S. Cl.
CPC ............ *A61B 8/0833* (2013.01); *A61B 8/406* (2013.01); *A61B 8/461* (2013.01); *A61B 8/466* (2013.01); *A61B 8/469* (2013.01); *A61B 8/483* (2013.01); *A61B 8/5207* (2013.01); *A61B 8/5223* (2013.01); *A61B 8/5238* (2013.01); *G06T 7/0014* (2013.01); *A61B 5/4312* (2013.01); *G06T 2207/10136* (2013.01); *G06T 2207/30068* (2013.01)

(56) References Cited

U.S. PATENT DOCUMENTS

| | | |
|---|---|---|
| 3,881,466 A | 5/1975 | Wilcox |
| 3,886,489 A | 5/1975 | Jones |
| 4,028,934 A | 6/1977 | Sollish |
| 4,059,010 A | 11/1977 | Sachs |
| 4,075,883 A | 2/1978 | Glover |
| 4,105,018 A | 8/1978 | Greenleaf et al. |
| 4,222,274 A | 9/1980 | Johnson |
| 4,317,369 A | 3/1982 | Johnson |
| 4,328,707 A | 5/1982 | Clement et al. |
| 4,431,008 A | 2/1984 | Wanner et al. |
| 4,433,690 A | 2/1984 | Green et al. |
| 4,509,368 A | 4/1985 | Whiting et al. |
| 4,515,165 A | 5/1985 | Carroll |
| 4,541,436 A | 9/1985 | Hassler et al. |
| 4,542,744 A | 9/1985 | Barnes et al. |
| 4,562,540 A | 12/1985 | Devaney |
| 4,564,019 A | 1/1986 | Miwa |
| 4,646,756 A | 3/1987 | Watmough et al. |
| 4,662,222 A | 5/1987 | Johnson |
| 4,671,256 A | 6/1987 | Lemelson |
| 4,733,562 A | 3/1988 | Saugeon |
| 4,855,911 A | 8/1989 | Lele et al. |
| 4,858,124 A | 8/1989 | Lizzi et al. |
| 4,917,096 A | 4/1990 | Englehart et al. |
| 4,941,474 A | 7/1990 | Pratt, Jr. |
| 5,003,979 A | 4/1991 | Merickel et al. |
| 5,029,476 A | 7/1991 | Metala et al. |
| RE33,672 E | 8/1991 | Miwa |
| 5,095,909 A | 3/1992 | Nakayama et al. |
| 5,103,129 A | 4/1992 | Slayton et al. |
| 5,143,069 A | 9/1992 | Kwon et al. |
| 5,158,071 A | 10/1992 | Umemura et al. |
| 5,178,147 A | 1/1993 | Ophir et al. |
| 5,179,455 A | 1/1993 | Garlick |
| 5,212,571 A | 5/1993 | Garlick et al. |
| 5,255,683 A | 10/1993 | Monaghan |
| 5,260,871 A | 11/1993 | Goldberg |
| 5,268,876 A | 12/1993 | Rachlin |
| 5,269,309 A | 12/1993 | Fort et al. |
| 5,280,788 A | 1/1994 | Janes et al. |
| 5,296,910 A | 3/1994 | Cole |
| 5,297,553 A | 3/1994 | Sliwa et al. |
| 5,304,173 A | 4/1994 | Kittrell et al. |
| 5,305,752 A | 4/1994 | Spivey et al. |
| 5,318,028 A | 6/1994 | Mitchell et al. |
| 5,329,817 A | 7/1994 | Garlick et al. |
| 5,339,282 A | 8/1994 | Kuhn et al. |
| 5,349,954 A | 9/1994 | Tiemann et al. |
| 5,413,108 A | 5/1995 | Alfano |
| 5,415,164 A | 5/1995 | Faupel et al. |
| 5,433,202 A | 7/1995 | Mitchell et al. |
| 5,463,548 A | 10/1995 | Asada et al. |
| 5,465,722 A | 11/1995 | Fort et al. |
| 5,474,072 A | 12/1995 | Shmulewitz |
| 5,479,927 A | 1/1996 | Shmulewitz |
| 5,485,839 A | 1/1996 | Aida et al. |
| 5,487,387 A | 1/1996 | Trahey et al. |
| 5,513,639 A | 5/1996 | Satomi et al. |
| 5,546,945 A | 8/1996 | Soldner |
| 5,553,618 A | 9/1996 | Suzuki et al. |
| 5,558,092 A | 9/1996 | Unger et al. |
| 5,573,497 A | 11/1996 | Chapelon |
| 5,582,173 A | 12/1996 | Li |
| 5,588,032 A | 12/1996 | Johnson et al. |
| 5,590,653 A | 1/1997 | Aida et al. |
| 5,596,992 A | 1/1997 | Haaland et al. |
| 5,606,971 A | 3/1997 | Sarvazyan |
| 5,609,152 A | 3/1997 | Pellegrino et al. |
| 5,620,479 A | 4/1997 | Diederich |
| 5,640,956 A | 6/1997 | Getzinger et al. |
| 5,643,179 A | 7/1997 | Fujimoto |
| 5,660,185 A | 8/1997 | Shmulewitz et al. |
| 5,664,573 A | 9/1997 | Shmulewitz |
| 5,673,698 A | 10/1997 | Okada et al. |
| 5,678,565 A | 10/1997 | Sarvazyan |
| 5,722,411 A | 3/1998 | Suzuki et al. |
| 5,743,863 A | 4/1998 | Chapelon |
| 5,749,364 A | 5/1998 | Sliwa, Jr. et al. |
| 5,759,162 A | 6/1998 | Oppelt et al. |
| 5,762,066 A | 6/1998 | Law et al. |
| 5,766,129 A | 6/1998 | Mochizuki |
| 5,797,849 A | 8/1998 | Vesely et al. |
| 5,800,350 A | 9/1998 | Coppleson et al. |
| 5,810,731 A | 9/1998 | Sarvazyan et al. |
| 5,817,025 A | 10/1998 | Alekseev et al. |
| 5,833,614 A | 11/1998 | Dodd et al. |
| 5,833,627 A | 11/1998 | Shmulewitz et al. |
| 5,846,202 A | 12/1998 | Ramamurthy et al. |
| 5,855,554 A | 1/1999 | Schneider et al. |
| 5,865,167 A | 2/1999 | Godik |
| 5,865,743 A | 2/1999 | Godik |
| 5,891,619 A | 4/1999 | Zakim et al. |
| 6,002,958 A | 12/1999 | Godik |
| 6,005,916 A | 12/1999 | Johnson et al. |
| 6,014,473 A | 1/2000 | Hossack et al. |
| 6,023,632 A | 2/2000 | Wilk |
| 6,050,943 A | 4/2000 | Slayton et al. |
| 6,056,690 A | 5/2000 | Roberts |
| 6,083,166 A | 7/2000 | Holdaway et al. |
| 6,102,857 A | 8/2000 | Kruger |
| 6,109,270 A | 8/2000 | Mah et al. |
| 6,117,080 A | 9/2000 | Schwartz |
| 6,135,960 A | 10/2000 | Holmberg |
| 6,149,441 A | 11/2000 | Pellegrino et al. |
| 6,242,472 B1 | 6/2001 | Sekins et al. |
| 6,245,017 B1 | 6/2001 | Hashimoto et al. |
| 6,256,090 B1 | 7/2001 | Chen et al. |
| 6,289,235 B1 | 9/2001 | Webber et al. |
| 6,292,682 B1 | 9/2001 | Kruger |
| 6,296,489 B1 | 10/2001 | Blass et al. |
| 6,317,617 B1 | 11/2001 | Gilhuijs et al. |
| 6,351,660 B1 | 2/2002 | Burke et al. |
| 6,368,275 B1 | 4/2002 | Sliwa et al. |
| 6,385,474 B1 | 5/2002 | Rather et al. |
| 6,413,219 B1 | 7/2002 | Avila et al. |
| 6,450,960 B1 | 9/2002 | Rather et al. |
| 6,475,150 B2 | 11/2002 | Haddad |
| 6,478,739 B1 | 11/2002 | Hong |
| 6,490,469 B2 | 12/2002 | Candy |
| 6,511,427 B1 | 1/2003 | Sliwa, Jr. et al. |
| 6,527,759 B1 | 3/2003 | Tachibana et al. |
| 6,540,678 B2 | 4/2003 | Rather et al. |
| 6,559,178 B1 | 5/2003 | Zamoyski |
| 6,574,499 B1 | 6/2003 | Dines et al. |
| 6,587,540 B1 | 7/2003 | Johnson et al. |
| 6,636,584 B2 | 10/2003 | Johnson et al. |
| 6,645,202 B1 | 11/2003 | Pless et al. |
| 6,672,165 B2 | 1/2004 | Rather et al. |
| 6,716,412 B2 | 4/2004 | Unger |
| 6,728,567 B2 | 4/2004 | Rather et al. |
| 6,776,760 B2 | 8/2004 | Marmarelis |
| 6,785,570 B2 | 8/2004 | Nir |
| 6,810,278 B2 | 10/2004 | Webber et al. |

(56) References Cited

U.S. PATENT DOCUMENTS

| | | | |
|---|---|---|---|
| 6,837,854 | B2 | 1/2005 | Moore et al. |
| 6,883,194 | B2 | 4/2005 | Corbell et al. |
| 6,926,672 | B2 | 8/2005 | Moore et al. |
| 6,939,301 | B2 | 9/2005 | Abdelhak |
| 6,984,210 | B2 | 1/2006 | Chambers et al. |
| 7,025,725 | B2 | 4/2006 | Dione et al. |
| 7,179,449 | B2 | 2/2007 | Lanza et al. |
| 7,285,092 | B2 | 10/2007 | Duric et al. |
| 7,346,203 | B2 | 3/2008 | Turek et al. |
| 7,497,830 | B2 | 3/2009 | Li |
| 7,530,951 | B2 | 5/2009 | Fehre et al. |
| 7,556,602 | B2 | 7/2009 | Wang et al. |
| 7,570,742 | B2 | 8/2009 | Johnson et al. |
| 9,144,403 | B2 | 9/2015 | Duric et al. |
| 2001/0029334 | A1 | 10/2001 | Graumann et al. |
| 2001/0037075 | A1 | 11/2001 | Candy |
| 2002/0065466 | A1 | 5/2002 | Rather et al. |
| 2002/0099290 | A1 | 7/2002 | Haddad |
| 2002/0131551 | A1 | 9/2002 | Johnson et al. |
| 2003/0138053 | A1 | 7/2003 | Candy et al. |
| 2004/0030227 | A1 | 2/2004 | Littrup et al. |
| 2004/0059265 | A1 | 3/2004 | Candy et al. |
| 2004/0152986 | A1 | 8/2004 | Fidel et al. |
| 2004/0167396 | A1 | 8/2004 | Chambers et al. |
| 2004/0181154 | A1 | 9/2004 | Peterson et al. |
| 2005/0165309 | A1 | 7/2005 | Varghese et al. |
| 2005/0196025 | A1 | 9/2005 | Schofield |
| 2005/0260745 | A1 | 11/2005 | Domansky et al. |
| 2006/0009693 | A1 | 1/2006 | Hanover et al. |
| 2006/0020205 | A1 | 1/2006 | Kamiyama |
| 2006/0064014 | A1 | 3/2006 | Falco et al. |
| 2006/0084859 | A1 | 4/2006 | Johnson et al. |
| 2006/0085049 | A1 | 4/2006 | Cory et al. |
| 2006/0287596 | A1 | 12/2006 | Johnson et al. |
| 2006/0293597 | A1 | 12/2006 | Johnson et al. |
| 2007/0015949 | A1 | 1/2007 | Kaiser |
| 2007/0167823 | A1 | 7/2007 | Lee et al. |
| 2008/0045864 | A1 | 2/2008 | Candy et al. |
| 2008/0218743 | A1 | 9/2008 | Stetten et al. |
| 2008/0229832 | A1 | 9/2008 | Huang et al. |
| 2008/0269812 | A1 | 10/2008 | Gerber et al. |
| 2008/0275344 | A1 | 11/2008 | Glide-Hurst et al. |
| 2008/0281205 | A1 | 11/2008 | Naghavi et al. |
| 2008/0294027 | A1 | 11/2008 | Frinking et al. |
| 2008/0294043 | A1 | 11/2008 | Johnson et al. |
| 2008/0319318 | A1 | 12/2008 | Johnson et al. |
| 2009/0035218 | A1 | 2/2009 | Ross et al. |
| 2009/0076379 | A1 | 3/2009 | Hamill et al. |
| 2009/0129556 | A1 | 5/2009 | Ahn |
| 2009/0143674 | A1 | 6/2009 | Nields et al. |
| 2010/0331699 | A1 | 12/2010 | Yu et al. |
| 2011/0152685 | A1 | 6/2011 | Misono |
| 2013/0267850 | A1 | 10/2013 | Berman |
| 2014/0316269 | A1 | 10/2014 | Zhang et al. |

FOREIGN PATENT DOCUMENTS

| | | | |
|---|---|---|---|
| EP | 351610 | A | 1/1990 |
| EP | 538241 | A | 4/1993 |
| EP | 0609922 | A | 8/1994 |
| EP | 661029 | A | 7/1995 |
| EP | 774276 | A | 5/1997 |
| EP | 1063920 | A | 1/2001 |
| JP | 2005253827 | A | 9/2005 |
| JP | 2007181679 | A | 7/2007 |
| JP | 2009034521 | A | 2/2009 |
| WO | 9947046 | A | 9/1999 |
| WO | 0230288 | A | 4/2002 |
| WO | 2002028350 | | 4/2002 |
| WO | 2004061743 | A | 7/2004 |
| WO | 2005057467 | A | 6/2005 |
| WO | 2007023408 | A | 3/2007 |
| WO | WO-2011100691 | A1 | 8/2011 |

OTHER PUBLICATIONS

PCT/US2011/024765 International Search Report and Written Opinion dated Jun. 16, 2011.

U.S. Appl. No. 13/027,036 Final Office Action dated Dec. 19, 2013.

U.S. Appl. No. 13/027,036 Non-Final Office Action dated Apr. 24, 2013.

U.S. Appl. No. 13/027,036 Non-Final Office Action dated Feb. 26, 2015.

U.S. Appl. No. 13/027,036 Non-Final Office Action dated Sep. 14, 2012.

U.S. Appl. No. 13/027,036 Notice of Allowance dated Jun. 23, 2015.

Palomares et al., "Mammographic Density Correlation with Gail Model Breast Cancer Risk Estimates and Component Risk Factors," Cancer Epidemiol Biomarkers Prey 15(7) (2006) 1324-1330.

Quan et al., Sound-speed tomography using first-arrival transmission ultrasound for a ring array, Medical Imaging 2007: Ultrasonic Imaging and Signal Processing, Proc. of SPIE vol. 6513.

Robinson et al., "Quantitative Sonography," Ultrasound in Med & Biol 12(7): 555-65 (1986).

Singh, Seema et al. "Color Doppler Ultrasound as an Objective Assessment Tool for Chemotherapeutic Response in Advanced Breast Cancer." Breast Cancer, 2005, vol. 12, No. 1, 2005, pp. 45-51.

Teubner et al., "Comparative Studies of Various Echomammography," Ultraschall in Der Medizin 3(3) (1982) 109-18, G. Thieme Verlag, Stuttgart/New York.

Vaezy et al., "Real-Time Visualization of High-Intensity Focused Ultrasound Treatment Using Ultrasound Imaging," Ultrasound in Med & Biol 27(1) (2001) 33-42.

Walach et al., Local Tissue Attenuation Images Based on Pulsed-Echo Ultrasound Scans, IEEE Transactions Onbiomedical Engineering, vol. 36. No. 2, Feb. 1989.

Wei et al., "Correlation Between Mammographic Density and Volumetric Fibroglandular Tissue Estimated on Breast MR Images," Med Phys 31(4) (2004) 933-942.

Weiwad et al., "Direct Measurement of Sound Velocity in Various Specimens of Breast Tissue," Invest Radiol 35(12) (2000) 721-6.

Wolfe, "Risk for Breast Cancer Development Determined by Mammographic Parenchymal Pattern," Cancer 37(5) (1976) 2486-2493.

Xu, et al. "A Study of 3-Way Image Fusion for Characterizing Acoustic Properties of Breast Tissue." Medical Imaging 2008: Ultrasonic Imaging and Signal Processing. Feb. 16, 2008.

Yaffe, "Breast Cancer Risk and Measured Mammographic Density," Eur J Cancer Prevention 7(1) (1998) S47-55.

Yaman, C. et al., "Three-Dimensional Ultrasound to Assess the Response to Treatment in Gynecological Malignancies." Gynecologic Oncology, Academic Press, vol. 97, No. 2, May 1, 2005, pp. 665-668.

Yankelevitz et al., "Small Pulmonary Nodules: Volumetrically Determined Growth Rates Based on CT Evaluation," Radiology 217 (2000) 251-256.

Zhang et al., A comparison of material classification techniques for ultrasound inverse imaging, J. Acoust. Soc. Am. 111 (1), Pt. 1, Jan. 2002.

Azhari et al., "Volumetric Imaging with Ultrasonic Spiral CT," Radial 212 (1999) 270-275.

Banihashemi, B. et al., "Ultrasound Imaging of Apoptosis in Tumor Response: Novel Preclinical Monitoring of Photodynamic Therapy Effects." Cancer Research, vol. 68, No. 20, Oct. 15, 2008, pp. 8590-8596.

Barlow et al., "Prospective Breast Cancer Risk Prediction Model for Women Undergoing Screening Mammogrpahy," J. Nat'l Cancer Institute 98(17): 1204-1214 (2006).

Boone et al., "Dedicated Breast CT: Radiation Dose and Image Quality Evaluation," Med Phys 221(3): 657-667 (2001).

Boston et al., "Estimation of the Content of Fat and Parenchyma in Breast Tissue Using MRI T1 Histograms and Phantoms," MRI 23: 591-599 (2005).

Boyd, "Quantitative Classification of Mammographic Densities and Breast Cancer Risk: Results from the Canadian National Breast Screening Study," J Nat'l Cancer Institute 87(9): 670-675 (1995).

(56) References Cited

OTHER PUBLICATIONS

Byng et al., The Quantitative Analysis of Mammographic Densities,: Phys Med Biol 39 (1994) 1629-1638.
Centerline, PortalVision section, Summer 2002 edition, published by Varian Medical Systems.
Chan et al., An Agglomeration Multigrid Method for Unstructured Grids, Contemporary Mathematics, vol. 218, 1998.
Chang et al., "Breast Density Analysis in 3-D Whole Breast Ultrasound Images," IEEE Proc 28th IEEE EMBS Annual International Conference (2006) 2795-2798.
Chang et al., Kirchhoff migration of ultrasonic images, Materials evaluation, V59, N3, 413-417, 2001.
Chelfouh et al., "Characterization of Urinary Calculi: in Vitro Study of 'Twinking Artifact' revealed by Color-Flow Sonography," AJR Am. J. Roentgenol. 171( 4) (1998) 1055-60.
Chen et al., "Projecting Absolute Invasive Breast Cancer Risk in White Women with a Model that Includes Mammographic Density," J. Nat'l Cancer Institute 98(17) (2006) 1215-1226.
Diederich et al., "The design of ultrasound applicators for interstitial hyperthermia," Ultrasonics Symposium, Proc IEEE 1993 Baltimore, MD, USA Oct. 31-Nov. 3, 1993, New York, NY, USA, 1215-1219.
Duric et al. "Computed Ultrasound Risk Evaluation," Barbara Ann Karmanos Cancer Institute. pp. 1-23. 2008.
Duric et al., "Detection of Breast Cancer with Ultrasound Tomography: First Results with the Computed Ultrasound Risk Evaluation (CURE) Prototype," Med Phys 34(2) (2007).
Dussik, "The Ultrasonic Field as a Medical Tool," Amer J Phys Med 33(1) (1954) 5-20.
Fjield et al., "A Parametric Study of the Concentric-Ring Transducer Design for MRI Guided Ultrasound Surgery," J. Acoust. Soc. America 100 (2) Pt. 1 (1996).
Gervias et al., "Renal Cell Carcinoma: Clinical Experience and Technical Success with Radio-frequency Ablation of 42 Tumors," Radiology 226 (2003) 417-424.
Glide et al., "Novel Approach to Evaluating Breast Density Utilizing Ultrasound Tomography," Med Phys 34(2) (2007) 744-753.
Glide, "A Novel Approach to Evaluating Breast Density Using Ultrasound Tomography," Dissertation Graduate School of Wayne State University (2007).
Glide-Hurst et al., "A Novel Ultrasonic Method for Measuring Breast Density and Breast Cancer Risk," Med Imaging 2008, Proc SPIE vol. 6920, 69200Q.
Glide-Hurst et al., "Volumetric breast density evaluation from ultrasound tomography images", Medical Physics, vol. 35, 2008, pp. 3988-3997.
Glide-Hurst, "A New Method for Quantitative Analysis of Mammographic Density," Med Phys 34(11) (2007) 4491-4498.
Greenleaf et al., "Artificial Cavitation Nuclei Significantly Enhance Acoustically Incuded Cell Transfection," Ultrasound Med & Biol 24 (1998) 587-595.
Greenleaf, "Computerized Tomography with Ultrasound," Proc IEEE 71(3) (1983) 330-337.
Hayashi, "A New Method of Measuring in Vivo Sound Speed in the Reflection Mode," J Clin Ultrasound 16(2) (1988) 87-93.
Jellins et al., "Velocity Compensation in Water-Coupled Breast Echography," Ultrasonics 11(5) (1973) 223-6.
Kaizer et al., "Ultrasonographically Defined Parenchymal Pattenrs of the Breast: Relationship to Mammographic Patterns and Other Risk Factors for Breast Cancer," Brit J Radiology 61(722) (1988) 118-24.
Karssemeijer, "Automated Classification of Parenchymal Patterns in Mammograms," Phys Med Biol 43 (1998) 365-378.
Kerlikowske et al., "Longitudinal Measurement of Clinical Mammographic Breast Density to Improve Estimation of Breast Cancer Risk," J. Nat'l Cancer Institute 99(5) (2007) 386-395.
Klimes, Grid Travel-time Tracing: Second-order Method for the First Arrivals in Smooth Media, PAGEOPH, vol. 148, Nos. 3/4,1996.
Kossoff et al., "Average Velocity of Ultrasound in the Human Female Breast," J Acoust Soc America 53(6) (1973) 1730-6.
Li et al., "Clinical Breast Imaging Using Sound-Speed Reconstructions of Ultrasound Tomography Data," Med Imaging 2008, Proc SPIE vol. 6920, 6920009.
Li et al., "In Vivo Breast Sound-Speed Imaging with Ultrasound Tomography", Ultrasound in Med & Biol., vol. 35, No. 10, 2009, pp. 1615-1628.
Li et al., Breast Imaging Using Transmission Ultrasound: Reconstructing Tissue Parameters of Sound Speed and Attenuation,2008 International Conference on BioMedical Engineering and Informatics, IEEE computer society, 708-712.
Li et al., Comparison of ultrasound attenuation tomography methods for breast imaging, Medical Imaging 2008: UltrasonicImaging and Signal Processing, Proc. of SPIE vol. 6920, 692015-(1-9), 2008.
Li et al., Refraction corrected transmission ultrasound computed tomography for application in breast imaging, Med. Phys. 37(5), May 2010, 2233-2246.
Louvar et al., "Correlation of Color Doppler Flow in the Prostate with Tissue Microvascularity," Cancer 1:83(1) (1998) 135-40.
Marias, "Automatic Labelling and Bi-Rads Characterisation of Mammogram Densities," Proc 2005 IEEE, Sep. 1-4, 2005, pp. 6394-6398.
Mast, "Empirical Relationships Between Acoustic Parameters in Human Soft Tissues," Acoust Research Letters Online, Nov. 16, 2000, pp. 37-42.
Masugata et al., "Relationship Between Myocardial Tissue Density Measured by Microgravimetry and Sound Speed Measured by Acoustic Microscopy," Ultrasound in Med & Biol 25(9) (1999) 1459-1463.
McCormick et al., Multigrid solution of a linearized, regularized least-squares problem in electrical impedance tomography, Inverse Problems 9, 1993, 697-713.
Metz, "Basic principles of ROC analysis"; Semin Nucl Med. Oct. 8, 1978 (4):283-98.
Metz, "Receiver Operating Characteristic Analysis: A Tool for the Quantitative Evaluation of Observer Performance and Imaging Systems"; J Am Coli Radiol 2006; 3: 413-422.
Metz, "ROC methodology in radiologic imaging"; Invest Radiol. Sep. 21, 1986 (9):720-33.
Miller et al., "Sonoporation of Cultured Cells in the Rotating Tube Exposure System," Ultrasound Med & Biol 25 (1999) 143-149.
Noble et al., "Spleen Hemostasis Using High-Intensity Ultrasound: Survival and Healing," J. Trauma Injury, Infection, and Critical Care 53(6) (2002) 1115-1120.
Oh et al., Multigrid Tomographic Inversion With Variable Resolution Data and Image Spaces, IEEE Transactions on Image Proessing, vol. 15, No. 9, Sep. 2006.
Ophir et al., "Elastography: Ultrasonic Estimation and Imaging of the Elastic Properties of Tissues," Proc Instn Mech Engrs 213(Part H) (1999) 203-233.

METHOD OF CHARACTERIZING THE PATHOLOGICAL RESPONSE OF TISSUE TO A TREATMENT PLAN

CROSS-REFERENCE TO RELATED APPLICATIONS

This application is a continuation of co-pending U.S. patent application Ser. No. 13/027,036, filed 14 Feb. 2011, which claims the benefit of U.S. Provisional Application No. 61/304,256 filed 12 Feb. 2010, both of which are incorporated in their entirety by this reference.

TECHNICAL FIELD

This invention relates generally to the medical field, and more specifically to an improved method of characterizing the pathological response of tissue to a treatment plan in the cancer treatment field.

BACKGROUND

Common treatments for cancer include removal of cancerous tumor tissue from the patient, radiation treatment, chemotherapy, or ablation interventions, but the most effective treatment or combinations of treatments typically varies from patient to patient. For example, not all cancer patients respond to certain treatments like chemotherapy and radiation treatment, and furthermore not all responsive cancer patients have equal success with these treatments. The success of a treatment for a patient is often not known until the end of the treatment or after a follow-up period after the treatment. However, it is advantageous to be able to accurately predict whether a patient will respond well to a treatment, particularly earlier in the treatment plan, to guide implementation of alternative regimens and/or to abort an unsuccessful treatment plan. Accurate and frequent evaluation of a tumor's response to treatment allows a physician to optimize the treatment plan for the patient, and potentially spare an unresponsive patient from unnecessary side effects from the treatment, such as the physical and emotional toll of chemotherapy-induced side effects. Monitoring the state of tumor tissue in a patient could theoretically be performed with repeated use of magnetic resonance imaging (MRI) or positron emission tomography (PET). However, these technologies are costly and may not be accessible in a community for repeated use, making them ill-suited for frequent evaluation of tumor tissue. Other technologies, such as X-rays, utilize ionizing radiation that precludes frequent use. Thus, there is a need in the medical field to create an improved method of characterizing the pathological response of tissue to a treatment plan. This invention provides such an improved method.

DESCRIPTION OF THE PREFERRED EMBODIMENTS

The following description of preferred embodiments of the invention is not intended to limit the invention to these preferred embodiments, but rather to enable any person skilled in the art to make and use this invention.

Figure 1:
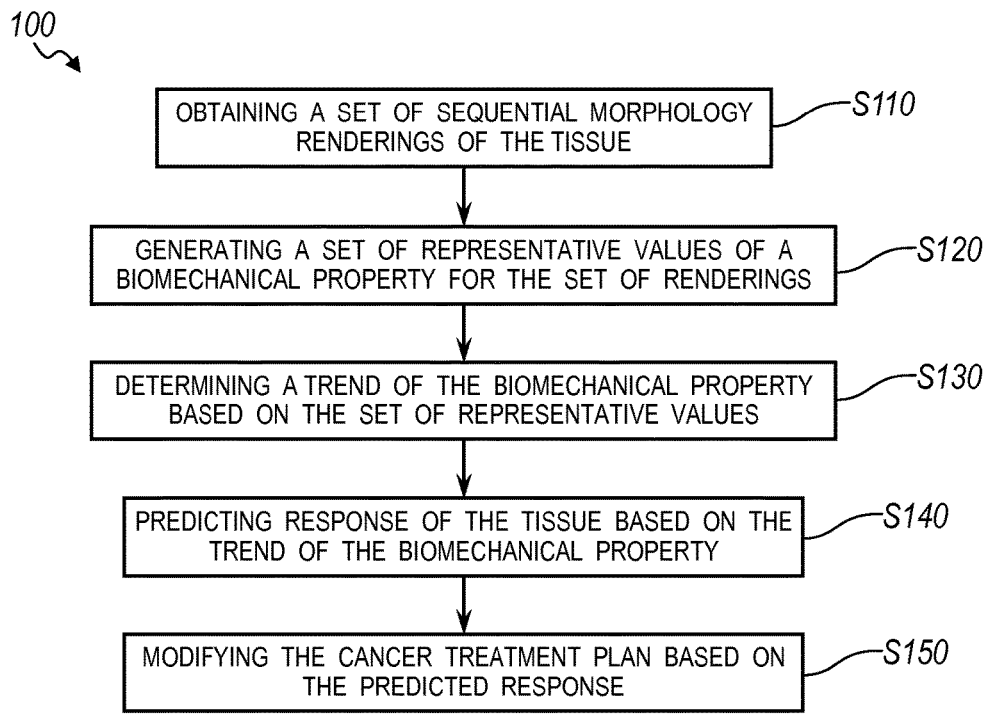
FIG. 1 is a schematic of the method of a preferred embodiment.

As shown in FIG. 1, the method 100 of characterizing the pathological response of tissue to a treatment plan of a preferred embodiment includes the steps of: obtaining a set of sequential morphology renderings of the tissue S110, wherein each rendering corresponds to a particular point in time during the treatment plan; generating a set of representative values of a biomechanical property of the tissue for the set of renderings S120, wherein each representative value is based on a corresponding rendering; determining a trend of the biomechanical property S130 based on the set of representative values; and predicting response of the tissue to the treatment plan S140 based on the trend of the biomechanical property. The method 100 is preferably used to predict and/or monitor the pathological response of cancer, such as breast cancer, to chemotherapy or radiation therapy (or side effects of the therapy), but may additionally and/or alternatively be used to predict or monitor the response of any cancer or benign tumors to any suitable treatment. The method 100 may additionally and/or alternatively be used to predict success of chemoprevention (a pharmacological approach to reducing cancer risk). Predicting and characterizing how a cancer patient will respond to a particular cancer treatment allows a physician to distinguish patients who are likely to have success with the treatment from those patients who are less likely to have success with the treatment, thereby allowing the physician to guide implementation of alternative regimens and/or to abort the particular treatment. Such knowledge about patient response to the treatment enables the physician to, for example, spare an unresponsive patient from suffering side effects of chemotherapy or radiation therapy and from applying potentially limited financial means towards an ineffective treatment, and move towards optimizing the efficacy of a treatment plan. The trend, such as rate of change, of the biomechanical property of the tumor early in the treatment plan is preferably used to predict the full treatment response, but the trend of the biomechanical property at any stage in the treatment plan may additionally and/or alternatively be used. The method 100 may facilitate an accurate and frequent evaluation of the tumor response to other therapies, such as to evaluate the clinical efficacy of a new therapeutic agent or regimen.

The step of obtaining a set of sequential morphology renderings S110 functions to obtain data from the patient. This data forms the basis of analysis in characterizing the response of the tissue to a cancer treatment. The morphology renderings preferably include renderings of tumor tissue, and may additionally and/or alternatively include renderings of healthy tissue such as that surrounding the tumor tissue. The morphology renderings may additionally and/or alternatively broken bones or any suitable tissue. Each rendering preferably corresponds to a particular point in time during the treatment plan, such that the set of renderings represent sequential, chronological snapshots of the tissue at various points in time during the treatment plan. For example, obtaining a rendering may be performed hourly, daily, every few days, every 1-3 weeks, or any suitable frequency, or performed in correspondence (e.g., immediately before and/or immediately after) a treatment phase such as a chemotherapy treatment. Obtaining a set of renderings S110 is preferably performed in early stages of a treatment plan (e.g., within the first several months), but may alternatively be performed during any suitable portion of the treatment plan. The set of renderings may be taken at approximately regular time intervals during the treatment plan, or at irregular time intervals (for example, the timing of the renderings may depend on particular scheduling of chemotherapy treatments). In a preferred embodiment, obtaining a set of renderings S110 preferably includes scanning the tissue with an ultrasound scanner to obtain acoustic data S112 and creating images representing acoustic parameters of the tissue with the acoustic data S114. The steps of scanning the tissue and creating images are each preferably performed at least once each time a single rendering is obtained, such that the steps of scanning the tissue and creating images are repeated multiple times. Obtaining a set of renderings S110 may additionally and/or alternatively include retrieving a set of images or renderings from a storage device such as a hard drive or an online server, or any suitable storage such as hard copy patient records.

Figure 2:
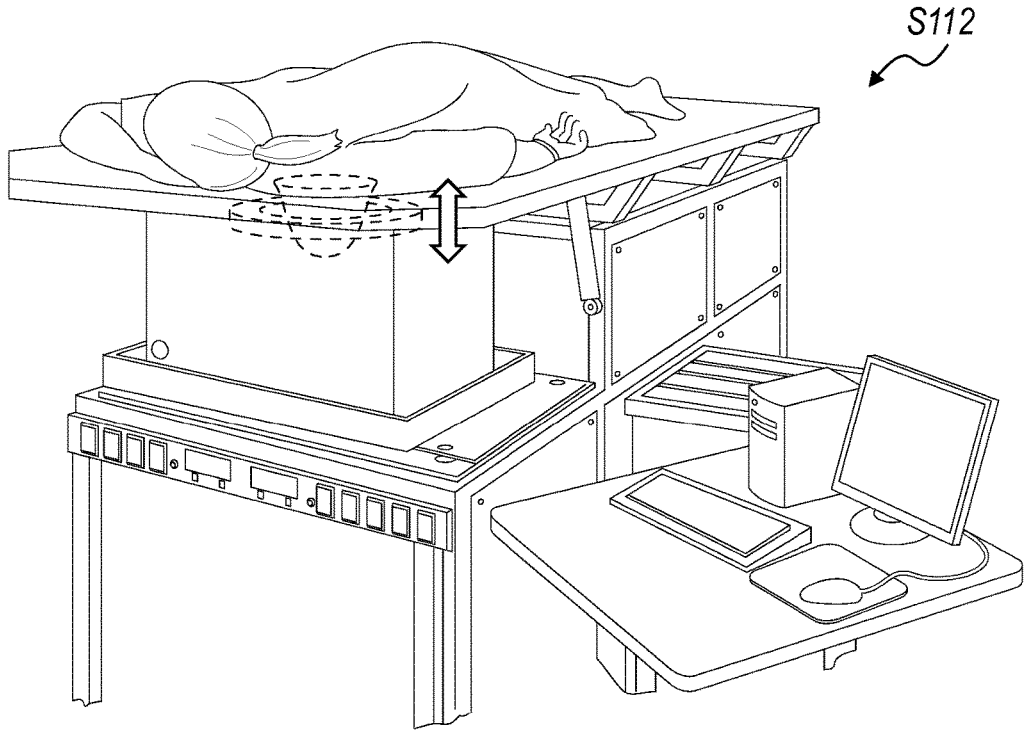
FIG. 2 is a schematic of a scanner that may be used during the step of obtaining a set of sequential morphological renderings of tissue in the method of a preferred embodiment.
Figure 3A:
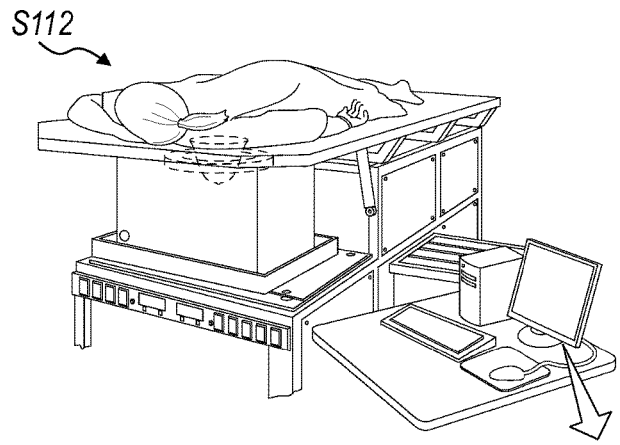
FIGS. 3A-3D are schematics of steps of obtaining a set of sequential morphological renderings of tissue in the method of a preferred embodiment.

The step of scanning the tissue S112 preferably includes surrounding the tissue with a transducer that transmits and receives acoustic waves through the tissue. For example, as shown in FIGS. 2 and 3A, to scan breast tissue of a breast cancer patient with an ultrasound tomography scanner having a ring-shaped transducer, the patient positions themselves face down on a flexible bed having a hole in the chest region of the bed. The breast of the patient passes through the hole in the bed and is positioned within the transducer immersed in a water bath. The ring transducer is preferably fixed to a gantry, and, during the scanning step S112, moves in a vertical path to pass between the chest wall and the nipple region in an anterior-posterior direction, thereby preferably imaging the entire breast (alternatively a selected portion of the breast). The scanner is preferably similar to that described in U.S. Patent Publication No. 2008/0275344 entitled "Method and apparatus for categorizing breast density and assessing cancer risk utilizing acoustic parameters", which is incorporated in its entirety by this reference. However, the ring transducer may be used to scan any suitable tissue, such as an arm, hand, leg, or foot. The scanner is preferably relatively inexpensive, quick, and more comfortable for the patient and easy to install and operate. The scanning step preferably gathers acoustic data including acoustic reflection from tissue, acoustic attenuation within tissue, and/or acoustic speed within tissue. However, the scanning step may additionally and/or alternatively gather any other acoustic data or suitable biomechanical property of the tissue. The method may alternatively include obtaining a set of morphology renderings using magnetic resonance imaging (MRI), positron emission tomography (PET), or any suitable device to generate renderings of tissue. For example, PET may be used to assess metabolic changes in tissue to generate tissue images.

Figure 3B:
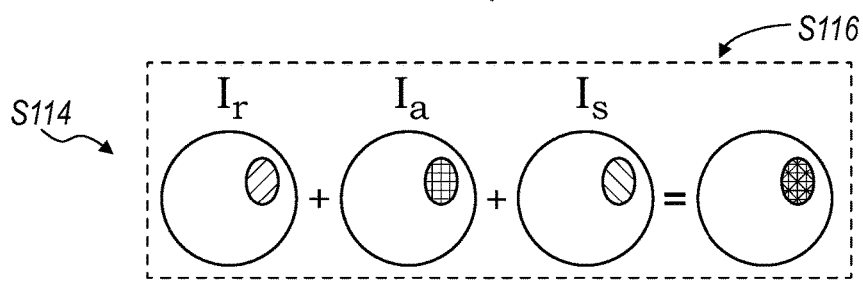
Figure 3C:
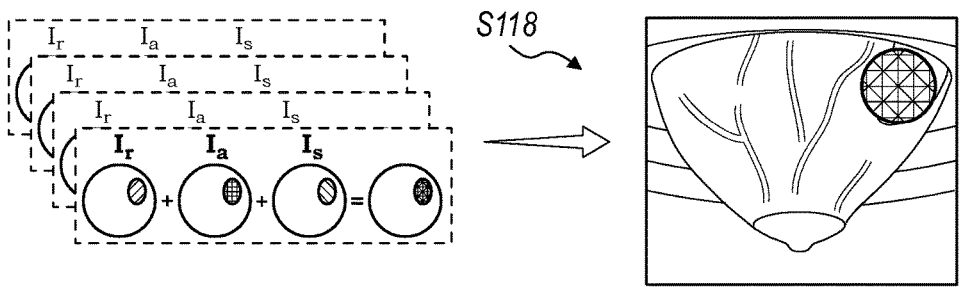
Figure 3D:
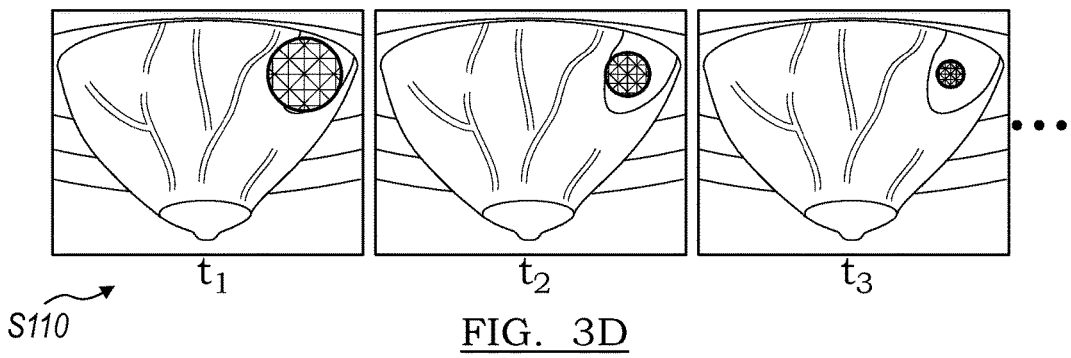

The step of creating images representing acoustic parameters of the tissue S114 preferably includes generating one or more two-dimensional (2D) images from the acoustic data obtained during the scanning step, and may include generating one or more three-dimensional (3D) images of the tissue. In a preferred embodiment, as shown in FIG. 3C, generating one or more 2D images includes generating a plurality of 2D cross-sectional images (e.g., "slices" in the coronal plane, or any suitable plane) of the tissue S116 and combining the 2D cross-sectional images of the tissue into a 3D image of the tissue S118. The images are preferably tomography images, and more preferably ultrasound tomography images, although they may alternatively be any suitable tomography images. A general process for combining stacks of 2D images into a 3D image is known by one skilled in the art, but one possible process is described in U.S. Patent Publication No. 2008/0275344. Alternatively, the 2D and/or 3D images may be generated in any suitable manner. As shown in FIG. 3D, in the step of obtaining a set of sequential morphology renderings S110, the steps of scanning and creating images are preferably repeated until a chronological set of renderings of the tissue (preferably 3D) are obtained, such that the set includes a morphological rendering at times t1, t2, t3 . . . to are obtained. The images preferably represent at least one of acoustic reflection from the tissue, acoustic attenuation within the tissue, and acoustic speed within the tissue. However, the images may additionally and/or alternatively represent any suitable biomechanical property of the tissue. For example, the images may represent the tissue under Doppler radar or the interaction of the tissue with a contrast agent (e.g., uptake or kinetics of flow). As shown in FIG. 3B, each acoustic parameter is preferably imaged in a separate stack of 2D images, such that at each cross-sectional level in the stack, the images for acoustic reflection (Ir), attenuation (Ia), and/or acoustic speed (Is) can be overlaid or combined into a merged 2D image.

Figure 4:
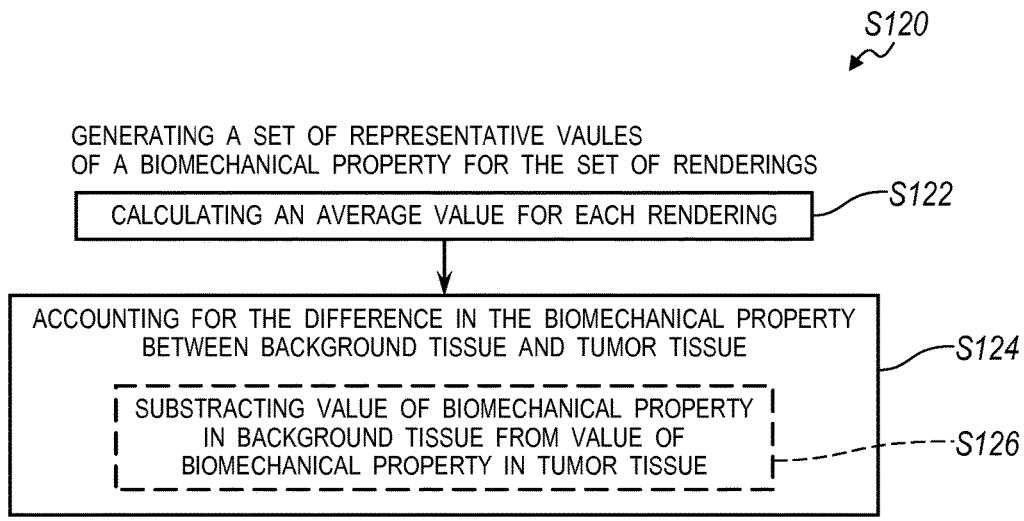
FIG. 4 is a schematic of the step of generating a set of representative values in the method of a preferred embodiment.
Figure 5:
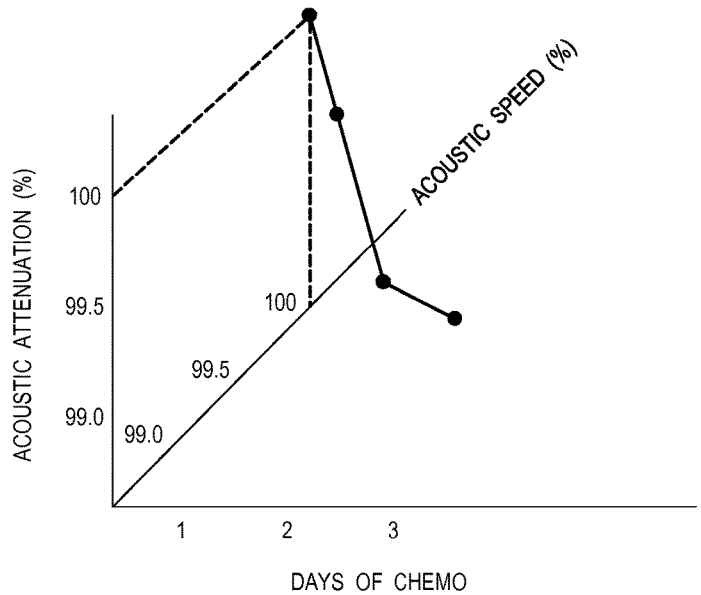
FIGS. 5 and 6 are schematics of variations of determining a trend of the biomechanical property based on a set of representative values of a biomechanical property in the method of a preferred embodiment.

The step of generating a set of representative values of a biomechanical property S120 functions to quantify or otherwise characterize the biomechanical property in the set of renderings. As shown in FIG. 4, the step of generating a set of representative values S120 preferably includes calculating an average value of the biomechanical property for each rendering S122, thereby generating a set of sequential or chronological volume average values of the biomechanical property of the tissue. Generating a set of representative values S120 may further include normalizing the set of representative values, such as to remove statistical error from the measured data. The generated representative values of the set of renderings are preferably of acoustic speed, but may additionally and/or include acoustic attenuation, acoustic speed, tissue density, and/or any suitable biomechanical property. In a preferred embodiment, the average value is a volume average of the biomechanical property in a primary tumor in the patient. The primary tumor is preferably defined by locating an outline of the tumor mass as it appears on the morphology renderings of the acoustic reflection image, and the tumor outline may be replicated on the acoustic attenuation and/or acoustic speed morphology renderings to show the boundary of the primary tumor. The volume average preferably incorporates the mean value of the biomechanical property within the volume of the primary tumor as characterized by the renderings. For example, an average volumetric acoustic speed may be calculated as described in U.S. Patent Publication No. 2008/0275344. However, the volume average may be a representative value of the biomechanical property in the primary tumor calculated in any suitable manner. For example, the volume average may additionally and/or alternatively include other aspects, such as being weighted by a spatial distribution of the values of the biomechanical property throughout the primary tumor. In another example, the volume average may take into account a combination of multiple different kinds of biomechanical properties throughout the primary tumor.

In one variation, the average value may be the mean or other statistical average of multiple volume averages of the multiple tumors, or the maximum volume average value of the multiple volume averages of multiple tumors. In another variation, the average value is the mean or other statistical average of any suitable healthy or unhealthy portion of the rendered tissue. However, the average value may alternatively be any suitable average value.

Calculating an average value of the biomechanical property for each rendering S122 preferably includes accounting for the difference between the value of the biomechanical property within the tumor tissue and the value of the biomechanical property in background tissue surrounding the tumor tissue S124. Accounting for the difference functions to disregard the value of the biomechanical property in the background tissue. Preferably, accounting for the difference S124 includes subtracting an average value of the biomechanical property in background tissue from the volume average value of the biomechanical property of the tumor tissue S126, but the difference may be accounted for in any suitable manner. The boundary of background tissue relative to tumor tissue in each rendering may be defined in one or more of several manners. In one variation, the background tissue may be defined as a region beyond a distance threshold (e.g., 2 centimeters) beyond the boundary of the outlined tumor tissue. In another variation, the background tissue may be defined as a region beyond a boundary where the gradient in the biomechanical property satisfies a difference threshold. However, the boundary of background tissue relative to tumor tissue may be defined in any suitable manner.

In another variation, generating a set of representative values S120 includes determining an initial or baseline value of the biomechanical property, or any suitable singular value of the biomechanical property. For instance, the initial value may be taken from the first rendering obtained in step S110. Furthermore, determining a trend of the biomechanical property S130 may include characterizing initial values of multiple biomechanical properties, or any suitable singular values of multiple biomechanical properties.

Alternatively, generating a set of representative values S120 may include characterizing the spatial distribution of the biomechanical property in each of the set of renderings. The characterization may be qualitative, or may be quantitative such as by generating a parameter descriptive of the spatial distribution of the biomechanical property. Generating a set of representative values S120 may include characterizing the spatial distribution of acoustic speed in an acoustic rendering, but may additionally and/or alternatively include characterizing the spatial distribution of acoustic attenuation or any suitable biomechanical property.

Figure 6:
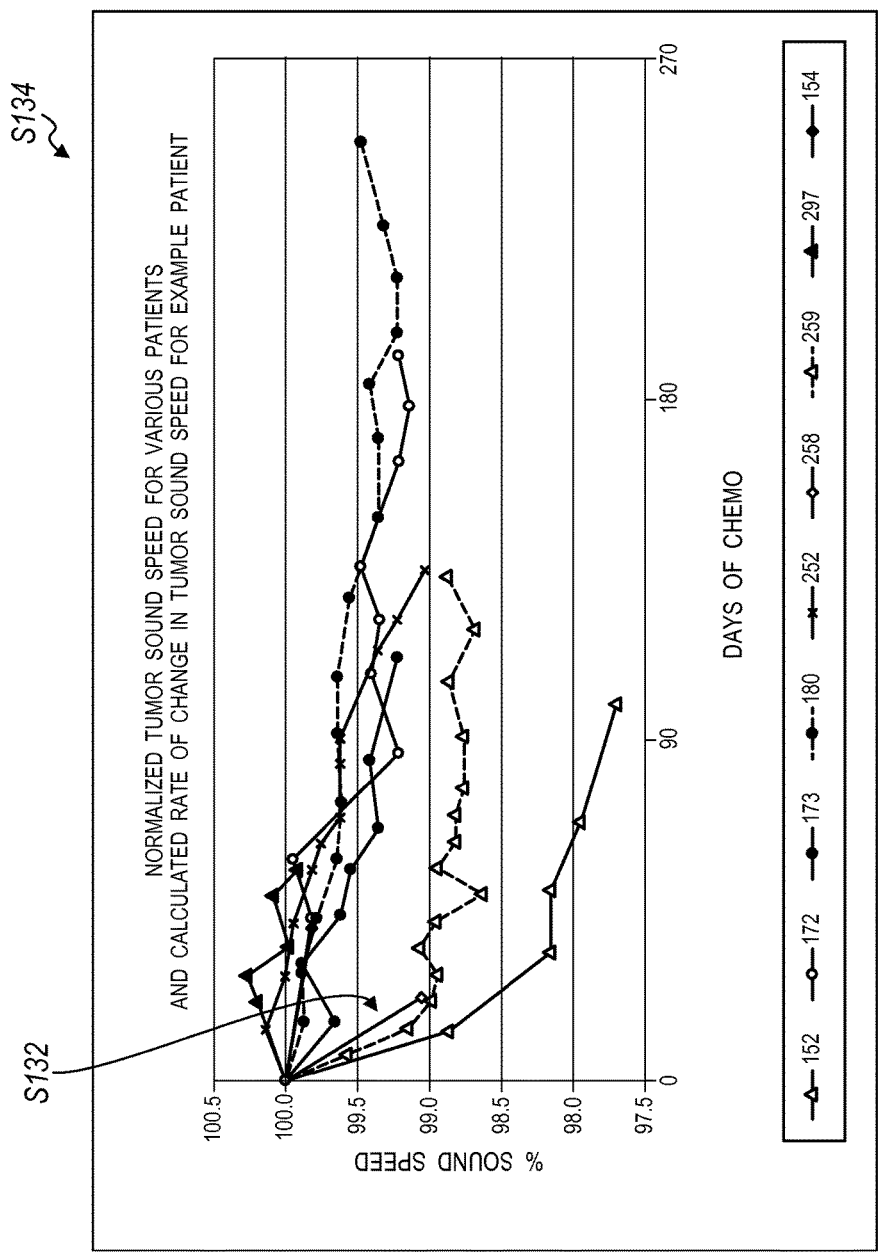

The step of determining a trend of the biomechanical property S130 functions to generate metrics, based on the acoustic data, that may be analyzed for predicting or otherwise characterizing patient response to a treatment plan. Determining a trend S130 preferably includes calculating a rate of change in the set of average values S132, which may be one or more of several variations. In a first variation, as shown in FIG. 6, determining a trend of the biomechanical property S130 includes graphing the set of average values of the biomechanical property on a plot against a temporal variable (e.g., number of days of treatment or number of treatments) S134. Each value of the set of average values may be expressed as an absolute value, expressed as a percentage of the first average value of the set, or in any suitable manner. In this variation, calculating a rate of change S132 preferably includes calculating a slope of a best-fit curve fitted to at least a portion of the plot. In other words, the calculated rate of change in the biomechanical property may be the slope of a best-fit curve fitted to two or more values in the set of volume average values. Alternatively, the calculated rate of change may be the slope between the first and last average values, the mean or median of slopes between subsets of adjacent pairs of average values, percentage difference between two or more points on the plots, or any suitable statistical measure of rate of change in the plot. The calculated rate of change may or may not be displayed on the plot.

In a second variation, determining a trend of the biomechanical property S130 includes mathematically calculating the rate of change. The calculation may be similar to the first variation except the computation is performed without graphing the set of average values on a plot.

In a third variation, determining a trend of the biomechanical property S130 includes determining a trend of multiple biomechanical properties. For example, initial values of multiple biomechanical properties may be characterized relative to each other, such as by plotting (or comparing in any suitable manner, such as by calculating a ratio) the initial value of one biomechanical property against another biomechanical property. For example, in determining a trend of multiple biomechanical properties, the initial value of acoustic speed of the tissue may be compared to the initial value of acoustic attenuation of the tissue. Furthermore, as shown in FIG. 6, multiple time-dependent representative values (e.g., chronological average values) of one biomechanical property may be compared to those of another biomechanical property, such as on a multi-dimensional plot having time-dependent values of acoustic speed on one axis, time-dependent values of acoustic attenuation on another axis, and potentially a temporal variable on a third axis, or on a plot having a ratio of two biomechanical properties on one axis and a temporal variable on another axis.

In an alternative embodiment, determining a trend of the biomechanical property S132 may include graphing the set of average values of the biomechanical property on a plot against a temporal variable, similar to the plot of the first variation, and characterizing the general shape of the curve formed by the plot. The general shape (e.g., a plateau) of the curve may be characterized quantitatively and/or qualitatively. For example, the trend of the biomechanical property shown on the plot may be described as having a certain type of slope or plateau indicating an approximately degree of gradient or flatness, respectively.

Figure 7:
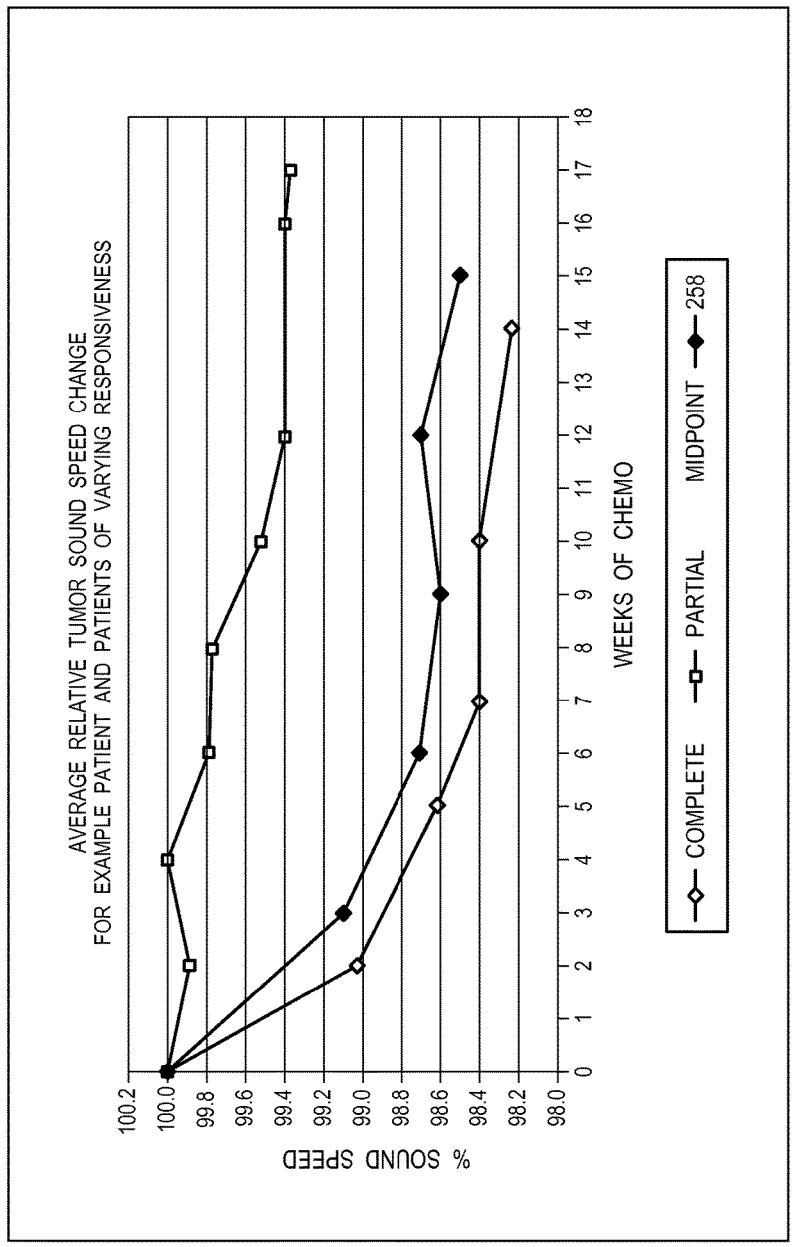
FIG. 7 is a schematic of one variation of predicting response of tissue to a treatment plan based on the trend of a biomechanical property in the method of a preferred embodiment.

The step of predicting response of the tissue S140 based on the trend of the biomechanical property functions to characterize the tissue response to the treatment plan. During the predicting step, the trend of the biomechanical property may be assessed for change in tissue properties, such as for long-term multiple stage intervention like chemotherapy and radiation therapy, or for cell death as a result of ablation interventions like cryotherapy, radiofrequency (RF) ablation, or electroporation. As shown in FIG. 7, predicting response of the tissue S140 preferably includes comparing the rate of change to a threshold S142. The threshold may be quantitative, or qualitative. The threshold is preferably based on data characterizing the response of prior patients to the treatment plan, such that prior patients undergoing the treatment plan form a baseline to which current patients may be compared. For example, thresholds may be determined with prior experimental data of patients who were scanned and analyzed according to the preferred method. Some or all of these prior patients may have completed the treatment plan, and additional means such as MRI or PET scans may have been used to determine whether these patients responded or did not respond to the treatment plan, and to what degree of success the responsive patients had with the treatment plan. Analysis of prior patients' experimental data may yield multiple thresholds that indicate varying thresholds of predicted responsiveness (e.g., "complete", "partial", or "nonresponsive") to the treatment plan.

In a preferred variation, the threshold may be a "success" threshold, such that if the rate of change (or any singular value, such as an initial baseline value) of the biomechanical property is at and/or above the success threshold, the patient is predicted to respond positively to the continued treatment plan. Furthermore, in this variation, if the rate of change does not meet the success threshold, then the patient is predicted to not respond favorably to the treatment. The exact comparison of the rate of change or other trend relative to the threshold depends on the specific biomechanical property. For example, if the rate of change in acoustic speed in a primary tumor in a particular patient is a declining slope that is steeper than the slope of the success threshold, then the particular patient is predicted to respond positively to the continued treatment plan. However, for other biomechanical properties, the patient may be predicted to respond positively if the rate of change is an inclining slope that is steeper than the slope of the success threshold. Alternatively, the threshold may be considered a "fail" threshold.

Predicting response of the tissue S140 may be additionally and/or alternatively include any suitable characteristic of the set of average values of the biomechanical property. For example, in one alternative variation, predicting response of the tissue S140 includes analyzing the general shape of the curve formed by a plot of the set of average values against a temporal variable. In another variation, predicting response of the tissue S140 includes analyzing the initial starting value of biomechanical property in the set of average values. In yet another variation, predicting response of the tissue S140 includes analyzing the trend of one or more biomechanical property and/or morphological characteristic relative to another biomechanical property and/or morphological characteristic. For example, analyzing the trend may include analyzing the spread or distribution of values on a multi-dimensional plot that has values of one biomechanical property (e.g., acoustic speed) on one axis, values of another biomechanical property (e.g., acoustic attenuation), and potentially a temporal variable on a third axis. In another example, analyzing the trend may include analyzing the trend of the ratio between two biomechanical properties (or general shape of the curve formed by a plot of the ratios against a temporal variable).

The method may further include modifying the treatment plan based on the predicted response S150, which functions to utilize the predicted response of the tissue to most benefit the patient. For example, if the prediction is that the patient will respond favorably to the treatment plan, then the step of modifying the treatment plan based on the predicted response S150 may include maintaining the current treatment plan and/or continuing to monitor the physiological response of the patient. As another example, if the prediction is that the patient will not respond favorably to the treatment, then the step of modifying the treatment plan may include: altering characteristics of the treatment plan (such as type of dose, dosage amount, dosage frequency, or distribution pattern of radiation or ablation), administering a different kind of treatment, or aborting the treatment plan. Other suitable modifications, dependent on the specific nature and status of the patient as known by one skilled in the art, may be at the physician's discretion.

As a person skilled in the art will recognize from the previous detailed description and from the figures and claims, modifications and changes can be made to the preferred embodiments of the invention without departing from the scope of this invention defined in the following claims.

We claim:

1. A method of characterizing pathological response of a tumor in a volume of tissue to a treatment plan, comprising:
    at a computing system in communication with an ultrasound system, generating a set of morphology renderings of the volume of tissue, from acoustic data received from the ultrasound system, wherein the set of morphology renderings is associated with a set of time points spanning at least a portion of the treatment plan;
    at the computing system, generating a set of volume average values of one or more biomechanical properties representative of a combination of acoustic speed with at least one of acoustic attenuation and acoustic reflection from the set of morphology renderings;
    at the computing system, calculating a rate of change in the one or more biomechanical properties for the tumor from the set of volume average values; and
    at the computing system, generating a predicted response of the tumor to the treatment plan based on the rate of change in the one or more biomechanical properties within the tumor.

2. The method of claim 1, wherein generating the set of morphology renderings includes suspending the volume of tissue within a bath having a ring transducer immersed in the bath, and passing the ring transducer along an anterior-posterior direction across the volume of tissue.

3. The method of claim 2, wherein generating the set of morphology renderings comprises 1) generating a plurality of two-dimensional cross-sectional images of the tumor and combining the cross-sectional images into a three-dimensional image of the tumor and 2) generating a merged image representing a combination of at least two of acoustic reflection, acoustic attenuation, and acoustic speed within the tumor.

4. The method of claim 1, wherein generating the set of volume average values includes generating at least one value based upon a combination of acoustic speed, acoustic attenuation, and acoustic reflection data for the tumor.

5. The method of claim 1, wherein calculating the rate of change in the biomechanical property within the tumor includes calculating a slope of a best-fit curve fitted to two or more values in the set of volume average values.

6. The method of claim 1, further comprising: at an output module of a user interface device in communication with the computing system, informing an entity of the predicted response, thereby enabling assessment of the treatment plan.

7. The method of claim 1, further comprising: by way of a display in communication with the computing system, automatically recommending an adjustment to the treatment plan, to an entity associated with a patient having the tumor, based upon a comparison between the rate of change in the biomechanical property and a success threshold slope.

8. The method of claim 7, wherein in automatically recommending the adjustment to the treatment plan, the success threshold slope is based upon a prior patient dataset characterizing response of prior patients to the treatment plan, wherein the prior patient dataset provides a set of thresholds indicative of predicted responsiveness to the treatment plan.

9. The method of claim 1, wherein the predicted response of the tumor to the treatment plan comprises an indication of the tumor as one of responsive, partially responsive, or nonresponsive.

10. The method of claim 1, wherein the set of time points is obtained at one or more phases of the treatment plan.

11. The method of claim 10, wherein at least one of the one or more phases comprises a treatment selected from the group consisting of a chemotherapy treatment, a radiation therapy treatment, a cryotherapy treatment, a radiofrequency ablation treatment, and an electroporation treatment.

12. The method of claim 10, wherein at least one of the set of time points is associated with at least one of the morphology renderings obtained immediately before or after at least one of the one or more treatment phases.

13. The method of claim 1, wherein a time point of the set of time points is obtained every one to three weeks.

14. The method of claim 1, wherein generating the set of volume average values comprises generating one or more volume average values characterizing tumor tissue and generating one or more volume average values characterizing background tissue.

15. The method of claim 1, wherein generating the predicted response of the tumor to the treatment plan comprises a qualitative characterization of the rate of change in the one or more biomechanical properties.

16. The method of claim 1, wherein generating the predicted response of the tumor to the treatment plan comprises a characterization of the rate of change in the one or more biomechanical properties and a characterization of a prior patient MRI or PET dataset.

17. The method of claim 1, wherein the method characterizes a pathological response of two or more tumors.

18. The method of claim 1, wherein the method further comprises characterizing a spatial distribution of the one or more biomechanical properties from the set of morphology renderings.

19. The method of claim 18, wherein generating the predicted response is additionally based on the spatial distribution of the one or more biomechanical properties.

20. The method of claim 1, wherein the method further comprises, at the computing system, graphing the set of volume average values of the one or more biomechanical properties on a plot against a temporal variable.

* * * * *

UNITED STATES PATENT AND TRADEMARK OFFICE
CERTIFICATE OF CORRECTION

PATENT NO. : 10,278,672 B2
APPLICATION NO. : 14/835349
DATED : May 7, 2019
INVENTOR(S) : Peter John Littrup and Nebojsa Duric It is certified that error appears in the above-identified patent and that said Letters Patent is hereby corrected as shown below:

In the Specification

In Column 1, Line 14, insert following header and paragraph:
--STATEMENT AS TO FEDERALLY SPONSORED RESEARCH
This invention was made with Government support under Grant R44CA165320 awarded by the National Institutes of Health (NIH) through the National Cancer Institute. The Government has certain rights in the invention.--

Signed and Sealed this
Sixth Day of August, 2024

Katherine Kelly Vidal
*Director of the United States Patent and Trademark Office*